(12) United States Patent
Rytky et al.

(10) Patent No.: US 6,183,422 B1
(45) Date of Patent: Feb. 6, 2001

(54) MEASURING SYSTEM

(75) Inventors: Pekka Rytky, Oulu; Seppo Korkala, Kempele, both of (FI)

(73) Assignee: Polar Electro Oy, Kempele (FI)

( * ) Notice: Under 35 U.S.C. 154(b), the term of this patent shall be extended for 0 days.

(21) Appl. No.: 09/257,661

(22) Filed: Feb. 25, 1999

(30) Foreign Application Priority Data

Mar. 2, 1998 (FI) ............................................ 980473

(51) Int. Cl.⁷ .............................................. A61B 5/0402
(52) U.S. Cl. ............................................................ 600/508
(58) Field of Search ................................ 600/508, 509, 600/485, 481

(56) References Cited

U.S. PATENT DOCUMENTS 4,527,096   7/1985   Kindlmann.

FOREIGN PATENT DOCUMENTS 68734   10/1985   (FI).
88972   7/1995   (FI).
5076502   3/1993   (JP).

OTHER PUBLICATIONS

European Patent Publication No. EPO 0 627 194 A2, published Dec. 7, 1994 Applicant: Telectronics N.V. (Same as U.S. Patent No. 5,404,877 to Nolan, et al.; issued Apr. 11, 1995).

Primary Examiner—Scott M. Getzow
(74) Attorney, Agent, or Firm—Hoffman & Baron, LLP

(57) ABSTRACT

The invention relates to a measuring system which measures the function of the heart from the user's body non-invasively. The measuring system comprises at least one functional unit which may be a transmitter unit attached particularly around the user's chest or a receiver unit worn on the wrist. The functional unit performs several functions by means of one of its induction coils (350): data transmission between two functional units, controlling of a sound signalling device (314), controlling of a light source (302) and charging of the power source.

12 Claims, 7 Drawing Sheets

MEASURING SYSTEM

FIELD OF THE INVENTION

1. Background of the Invention

The invention relates to a measuring system which measures the function of at least one organ from the user's body non-invasively and comprises at least one functional unit, such as a transmitter unit and/or a receiver unit.

2. Description of the Prior Art

Vital functions can be measured telemetrically using a non-invasive measuring device. An example of such a measuring device is a system which measures human heart rate and usually comprises such functional units as a transmitter unit, receiver unit and data transmission unit. The transmitter unit means a unit which is provided with electrodes and is held against the human body, particularly against the chest. This unit is often implemented as a transmitter belt attached around the body. The receiver unit refers to a watch-like unit which is worn on the wrist, for example, and which communicates telemetrically with the transmitter unit. The data transmission unit is used for transmitting data collected in the receiver unit to a computer, for example. The computer can also be used for controlling both the transmitter and the receiver units via the data transmission unit.

Measurement of the heart rate is based on monitoring the function of the heart. When the heart muscle contracts, it causes a series of electric impulses which can be measured in the body. The measurement and analysis of this signal is known as electrocardiography (EKG). The signal itself is called an EKG signal. Different phases of the heart cycle can be discerned in the EKG signal. These are called P, Q, R, S, T and U waves.

The unit that receives the heart rate usually comprises a piezoelectric sound signalling device, electroluminescent light source and at least a receiver for the heart rate. For the function of each device the prior art solutions comprise a separate induction coil. It is only known to use the same induction coil of the receiver unit for receiving the heart rate from the transmitter unit and for serial traffic with the data transmission unit. Since the receiver unit, in particular, is typically a device similar to a wrist watch, the space needed for several coils constitutes a major problem. The use of several coils also raises the price of the device.

OBJECTS AND SUMMARY OF THE INVENTION

The object of the invention is to provide a measuring system in which the above-mentioned problems are eliminated. Thus the space required by the coils can be reduced and the printed circuit simplified in the measuring system.

This is achieved with a measuring system described in the preamble, which is characterized in that the functional unit comprises an induction coil, whose inductive activity is arranged to be used for more than one function of the functional unit, the functions comprising inductive interaction between two functional units, controlling of a sound signalling device and controlling of a light source.

The system of the invention provides several advantages. Since the number of induction coils is reduced, less space is needed for electronic circuits. The coil is connectable to the desired function without the function having harmful effects on the other functions of the coil. The material costs also decrease.

BRIEF DESCRIPTION OF THE FIGURES

The invention will be described in greater detail by means of preferred embodiments with reference to the accompanying drawings, in which.

DETAILED DESCRIPTION OF THE PREFERRED EMBODIMENTS

The solution of the invention is particularly suitable for use in a measuring system which measures the heart pulse non-invasively.

Figure 1:
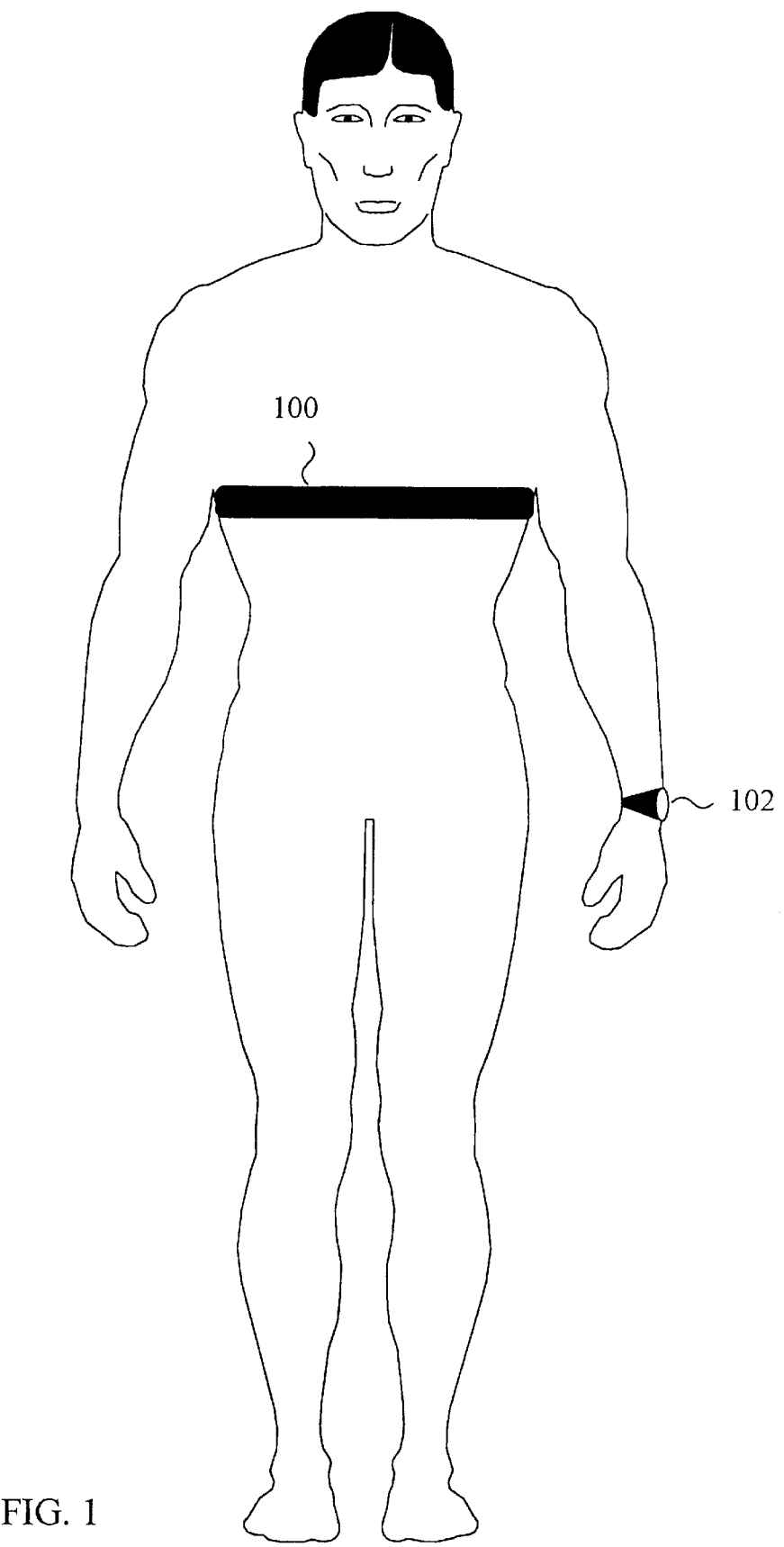
FIG. 1 illustrates a user wearing a measuring device.

FIG. 1 illustrates a preferred embodiment of the present invention, i.e. a heart rate meter. The heart rate meter comprises a transmitter unit 100 which is attached around the user's chest and measures the heart rate. The user also wears a receiver unit 102 of the system on his wrist, for example.

The measuring part, which comprises a transmitter unit and a receiver unit, may also have a one-piece structure in which case the heart rate meter is worn on the wrist and the heart rate is measured from the wrist. The transmitter unit may also be an independent device which stores the measurement data in its memory. After the exercise the measurement data can be unloaded to a computer, for example. Using the modern technology a better measuring result is, however, achieved with a solution described above in which the measuring part is divided into two parts: a wireless transmitter unit 100 which measures the heart rate and is attached around the user's chest and a receiver unit 102 which the user wears on his wrist.

Figure 2:
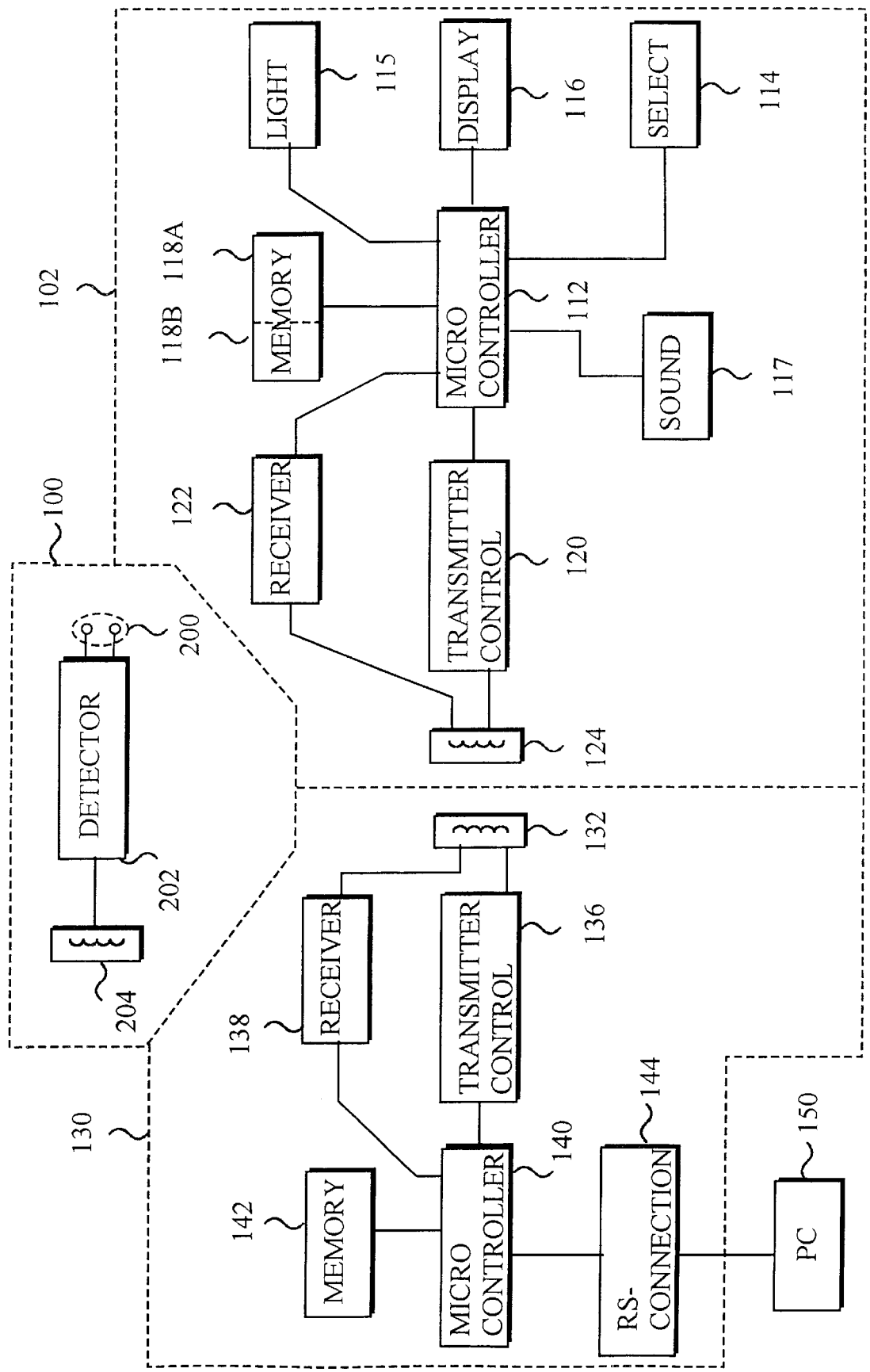
FIG. 2 illustrates a system which measures the heart rate.

FIG. 2 illustrates a system which uses telemetric data transmission for measuring the heart rate. The main parts of the system are a telemetric transmitter unit 100, telemetric receiver unit 102 and data transmission unit 130. The efficiency of data processing may be increased by using a data processing and controlling unit 150, which may be e.g. a PC. In the embodiment of FIG. 2 a transmission unit 100 known per se can be used, the unit comprising EKG electrodes 200, a block 202 for pre-amplifying the EKG and detecting the pulse and inductance 204. The output received from the block 202 is a heart rate signal controlling the inductance 204. The interval between the pulses of the heart rate signal is preferably the same as the interval between the heart beats. Thus a magnetic field alternating at the same rate as the heart rate is generated to the inductance 204, which inductively interacts, i.e. is inductively active, e.g. with the induction coil 124 of the receiver through the magnetic field. When the transmitter unit 100 is an independent device, i.e. the measuring system functions preferably without a receiver unit 102, the transmitter unit 100 may, like the receiver unit 102, comprise for example sound signalling blocks or other blocks which require inductive activity.

The receiver unit 102 comprises a control part 112. The control part 112 also controls a user interface which comprises selection means 114 and display means 116. The selection means 114 is typically a keyboard by means of which the user employs the receiver unit 102. The display means 116, such as an LCD display, conveys visual information to the user. The receiver unit typically also comprises a light source 115 for illuminating the display 116 and a sound signalling device 117. The control part 112 is typically a microprocessor which comprises a ROM memory 118A in which the software controlling the device is stored. The device may also contain additional memory 118B in which the data gathered during the measuring can be stored, e.g. information on the heart rate, time and other user-specific parameters. The control part 112 may also be implemented by using an ASIC circuit or other switching consisting of HW parts. The receiver 102 further comprises a transmission controller 120, receiver means 122 and inductance 124. The transmission controller 120 generates data transmission from the receiver unit 102 to the data transmission unit 130 using the inductance 124. By means of the inductance 124 the receiver means 122 receives information in the form of induced voltage from the inductance 132 of the data transmission unit 130 and converts it to a digital form for the microprocessor 112. The inductance 124, such as a coil, is excited to resonance by means of a capacitor (not shown) using the frequency employed for data transmission. When the receiver unit 102 is an independent device, i.e. no transmitter unit 100 is used, the receiver unit 102 naturally comprises a sensor (not shown) for measuring the function of the desired organ. The sensor whose function is not essential to the invention may be for example an optical sensor or its function may be based on measuring the pressure.

The data transmission unit 130 comprises an inductance 132, transmission controller 136, receiver means 138, computing unit such as a microprocessor 140, memory 142 and interface 144. The data transmission unit 130 communicates with the data processing unit 150, such as a PC, via the interface 144. The inductance 132 of the data transmission unit 130 is at the same resonance frequency as the inductance 124 of the receiver unit. The purpose of the transmission controller 136 is to generate a control signal for the inductance 132. The purpose of the receiver means 138 is to receive incoming serial data from the inductance 124 via the inductance 132. The microprocessor 140 converts the transmitted data to a suitable form for the PC (data processing unit 150). The memory 142 of the data transmission unit 130 may store files that have been read, if necessary. The interface 144, such as RS232, converts the voltage levels to suit the interface that is used.

Switching of the receiver unit 102 will now be described in greater detail with reference to FIGS. 3 to 7. The receiver unit comprises a light source 302 based on electroluminescence, light source controller 304, display component 306, pole 308 of a DC power source, switches 310, 312, 322, 324, 334, 336, sound signalling device 314, controller 316 of the sound signalling device, microprocessor 318, reception amplifier 320, receiver 326, controller 330 of the switches, transmission controller 332 and one induction coil 350. The switches 310, 312, 322, 324, 334, 336 are preferably voltage-controlled or current-controlled transistor switches, such as BJTs (Bipolar Junction transistor) or FETs (Field Effect Transistor). The switches 310, 312, 322, 324, 334, 336 are driven to a conducting state by supplying the control current or control voltage to the base or gate of the transistor, as is obvious to a person skilled in the art.

Figure 3:
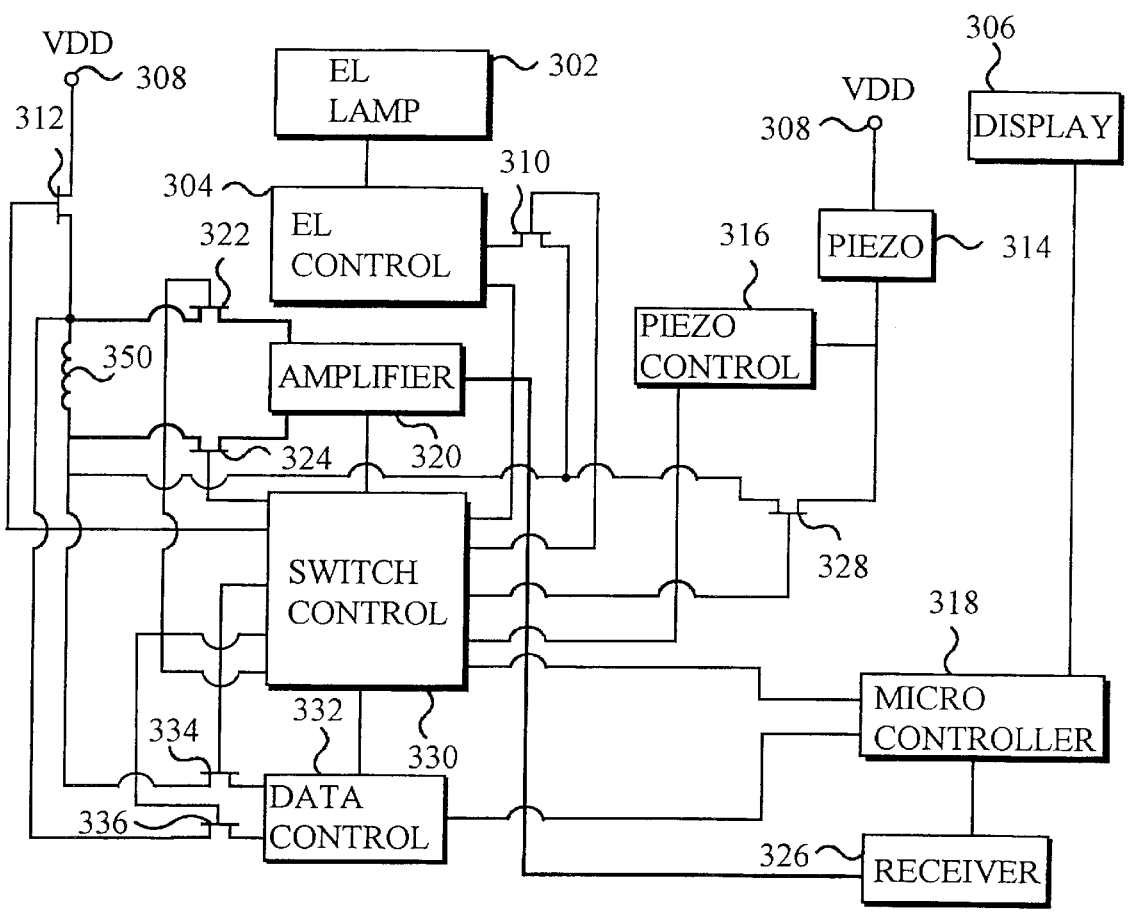
FIG. 3 illustrates active function of a receiver unit during reception.

In FIG. 3 the receiver unit is set to the reception mode. In that case the switch controller 330 drives the switches 322 and 324 to a conducting state, and thus the impedance of the switches 322 and 324 is small, and keeps the other switches 310, 312, 334, 336 in a high-impedance state, i.e. open. Thus the induction coil 350 is connected to the reception amplifier 320 via the switches 322 and 324, and the amplifier amplifies a signal induced in the induction coil 350. From the amplifier 320 the signal is supplied to the receiver 326 and further to the microprocessor 318 for data processing.

Figure 4:
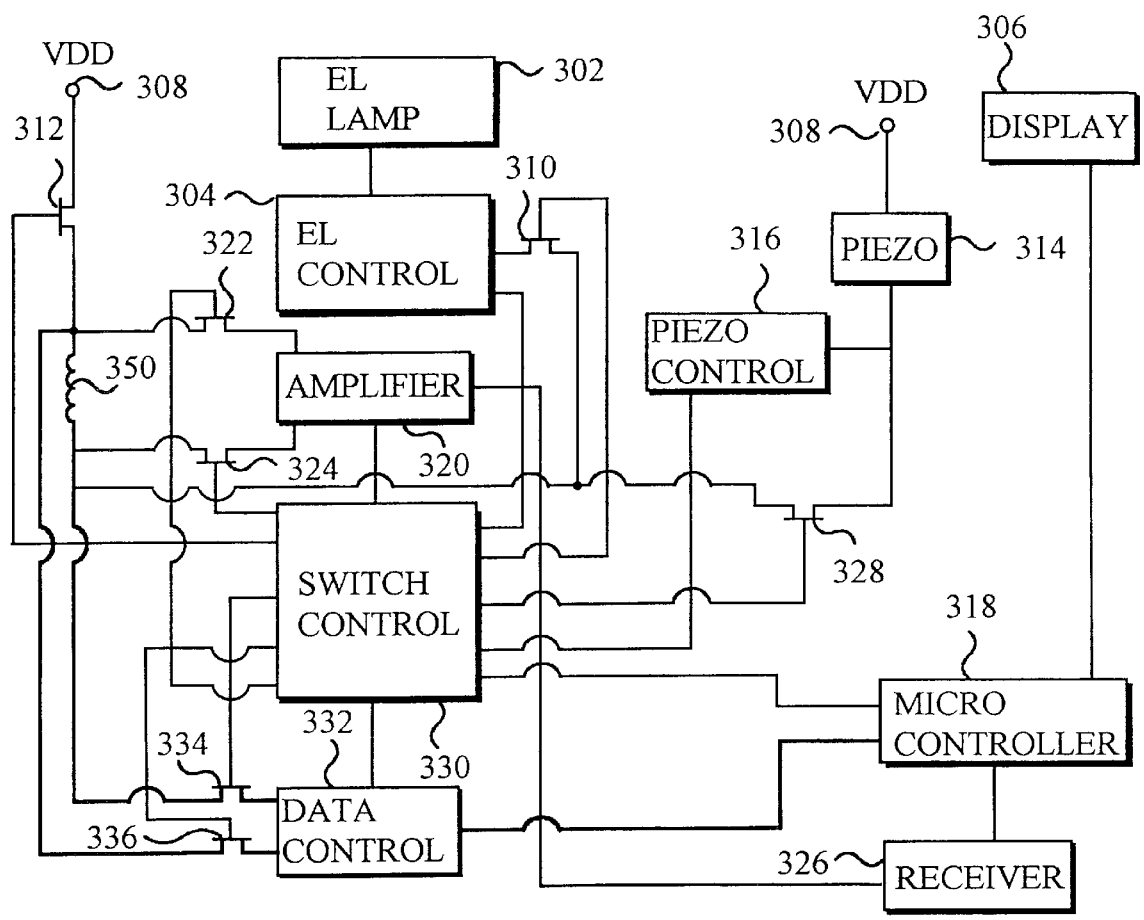
FIG. 4 illustrates active function of the receiver unit during transmission.

In FIG. 4 the receiver unit is set to the transmission mode, in which case the switch controller 330 drives the switches 334 and 336 to a conducting state and keeps the other switches 310, 312, 322, 324 open. The microprocessor 318 sends data to the transmission controller 332, which feeds the signal formed from the data to the induction coil 350 via the switches 334 and 336. The transmission controller 332 converts the input data from the processor 318 preferably to a serial form bit stream signal. The induction coil 350 radiates the signal as changes of the magnetic field to its surroundings.

Figure 5:
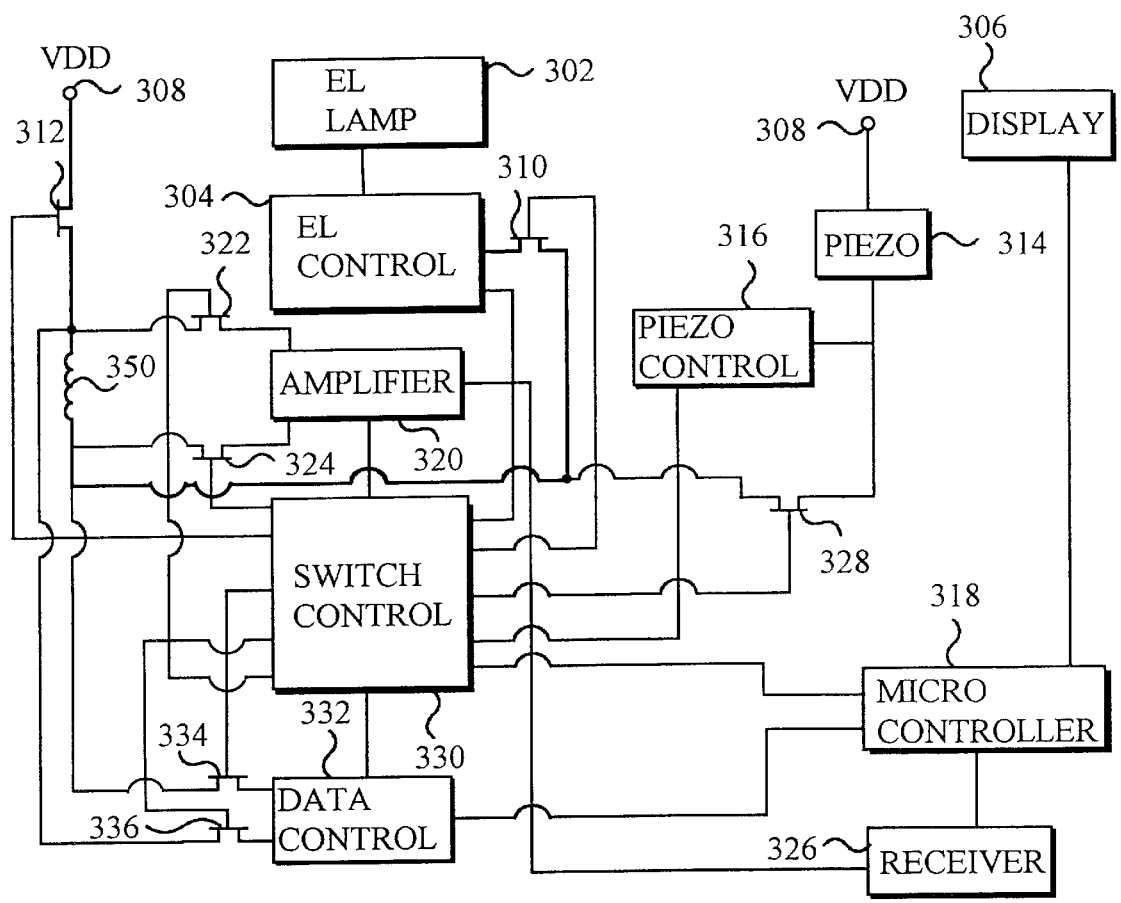
FIG. 5 illustrates active function of a light source of the receiver unit.

In FIG. 5 the light source 302 of the receiver unit is switched on. The switch controller 330 drives the switches 312 and 310 to a conducting state and keeps the other switches 322, 324, 334, 336 open. The pole 308 of the power source is connected to the pole of the induction coil 350 via the switch 312 and the other pole of the induction coil is connected to the light source controller 304 via the switch 310. Since the light source is preferably a component based on electroluminescence, an AC voltage of at least several dozen volts (e.g. 50 to 150 V) and typically of hundreds of hertz is needed to drive it. The controller 304 generates this voltage by means of the induction coil 350 in a manner obvious to a person skilled in the art. This prior art solution is disclosed for example in U.S. Pat. No. 4,527,096 which is incorporated herein as a reference. In the solution according to U.S. Pat. No. 4,527,096 the IC circuit uses the coil for producing the AC voltage required by the electroluminescence component. Thus the light source controller 304 generates the required AC voltage of dozens to hundreds of hertz by means of a resonance circuit which is produced by the induction coil 350. Even though this is not illustrated in FIG. 5, the both ends of the induction coil 350 are also connectable to the light source controller 304 if the controller 304 operates in this kind of wiring.

Figure 6:
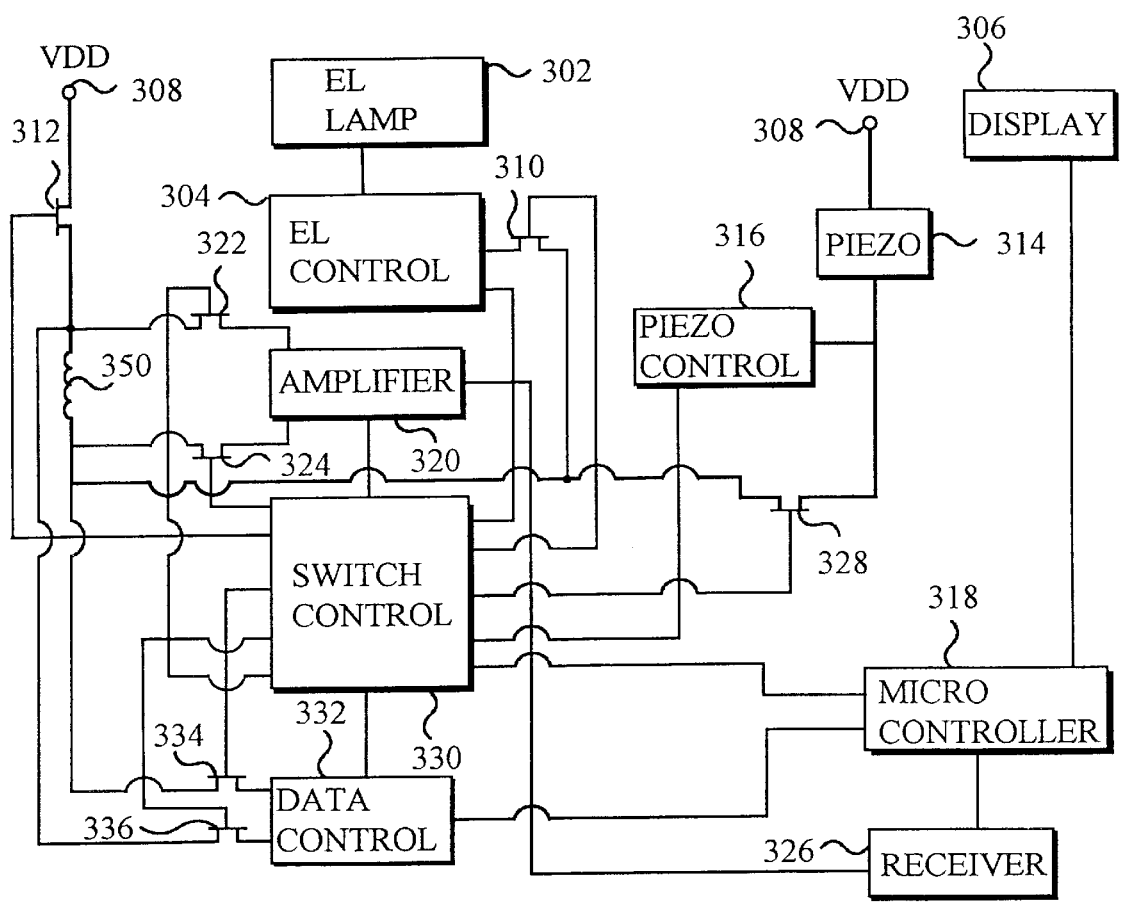
FIG. 6 illustrates active function of a sound signalling unit of the receiver unit.

In FIG. 6 the sound signalling device of the receiver unit is switched on. The switch controller 330 drives the switches 312 and 328 to a conducting state and keeps the other switches open. The induction coil 350 and sound signalling device 314, which is preferably a piezoelectric device, are connected to the pole 308 of the power source via the switches 312 and 328. The controller 316 of the sound signalling device generates an audio frequency resonance circuit by means of the induction coil 350 for example in such a manner that instantaneous DC voltage is connected to the induction coil 350, in which case the resonance circuit produced by the induction coil 350 and the piezoelectric sound signalling device 314 generates an alternating voltage which has a higher effective value than the operating voltage, and the resonance circuit oscillates at the frequency determined by the resonance. The electric resonance produced causes a piezoelectric crystal to resonate mechanically, which is heard as a sound.

Figure 7:
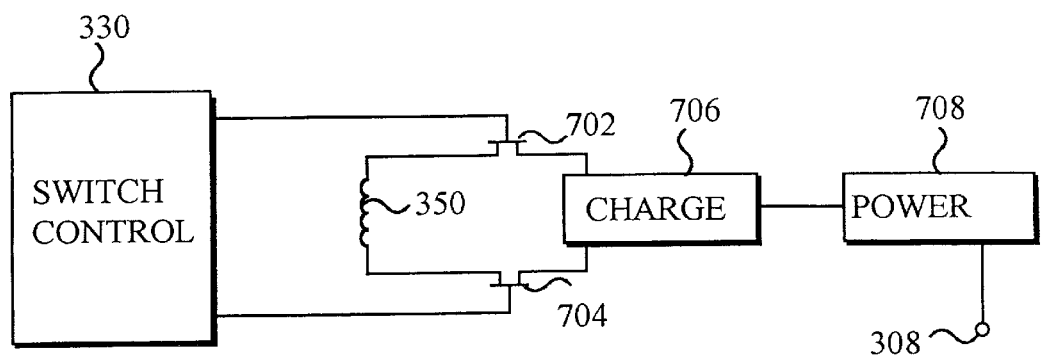
FIG. 7 illustrates charging of a power source of the receiver unit.

In FIG. 7 the power source 708 of the receiver unit is connected to charging. The structure of the receiver is substantially similar to that illustrated in FIGS. 3 to 6, but in FIG. 7 the structure has been simplified by omitting components that are not related to charging. The operating voltage VDD is obtained from the pole 308 of the power source 708. The power source 708 is charged as follows: the switch controller 330 drives switches 702 and 704 to a conducting state, and the induction coil 350 is connected to a charging circuit 706, which charges the power unit 708 with the energy received by the induction coil 350 via the switches 702 and 704. The induction coil 350 receives charging energy by means of mutual inductance from a separate charging device (not shown) which comprises a charging coil (not shown). The charging device feeds electric charging energy into its charging coil, from which charging energy is transferred to the induction coil 350 by means of mutual inductance.

Figure 8:
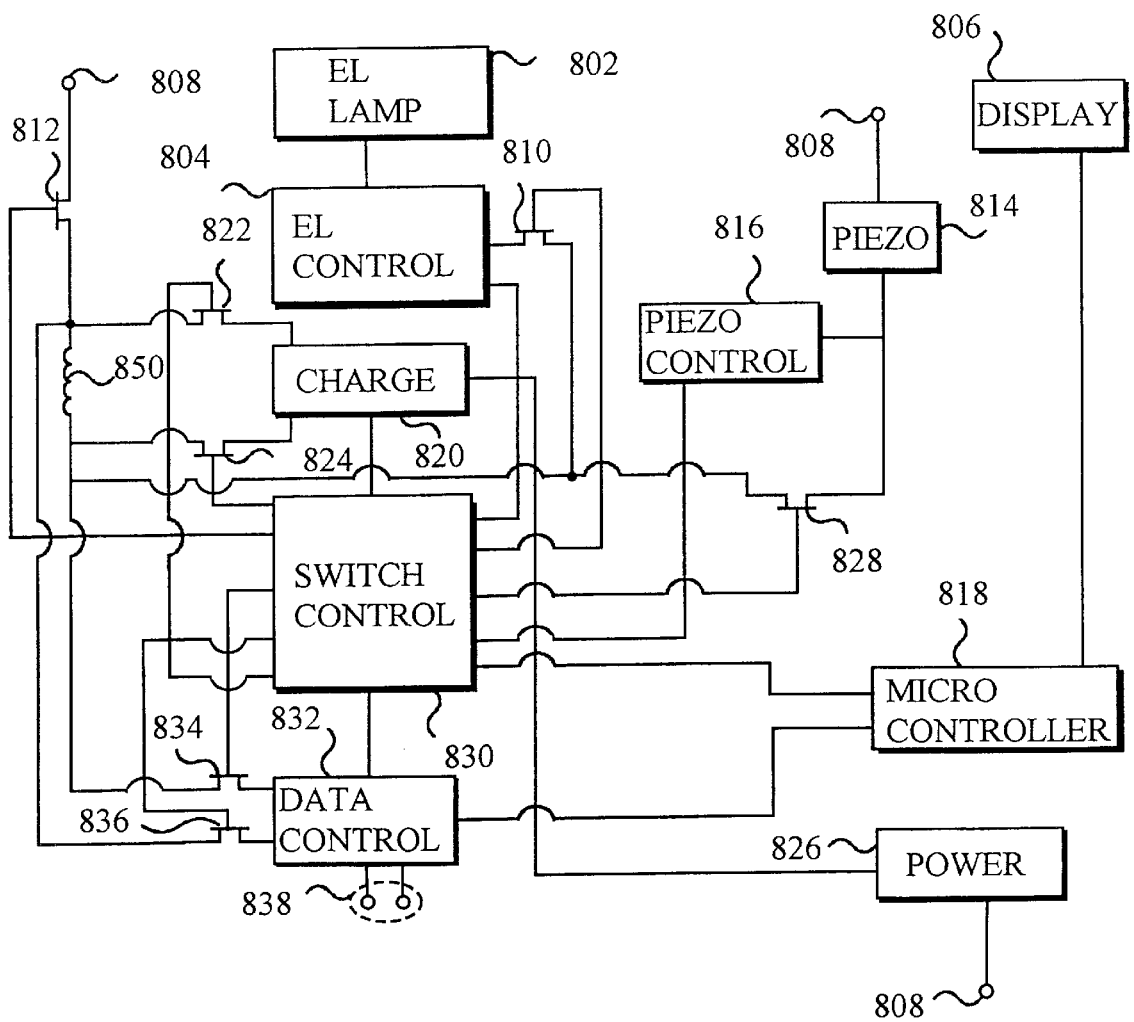
FIG. 8 illustrates charging of a power source of the transmitter unit.

FIG. 8 illustrates a switch diagram. The switch diagram is similar to that of the receiver unit. The units and tens of the reference numerals correspond to those used in connection with the receiver unit, but in the diagram of the transmission unit the reference numerals begin with a different number, i.e. the reference numerals are larger than 800. The transmitter unit differs from the receiver unit in that there is no amplification block 320 or receiver block 326. Instead of these the transmitter unit comprises blocks which enable charging, i.e. a block which receives 820 the charging energy and a power source 826, pole 808 being one of its poles. When charging begins, switches 822 and 824 are closed, and thus the charging energy to the coil 850 is supplied to the charging circuit 820 implemented in a manner obvious to a person skilled in the art. The charging circuit 820 feeds the charging energy further into the power source 826 to be charged. The smallest possible transmitter unit comprises only measuring electrodes 838 and a block 832 which at its simplest would be only a block for preamplification and pulse detection connected directly to the induction coil 850. In the switching according to FIG. 8 the following components have been added to the transmitter unit: a display 806, display illumination blocks 802 and 804, which form together a display block, blocks 816 and 808 for the sound signalling device, which form together a sound signalling block, and charging block 820. These blocks may be individually included in the transmitter unit or omitted from it.

The components used in the inventive solution are conventional prior art electronic, optoelectronic or mechanical components which are obvious to a person skilled in the art.

Even though the invention has been described with reference to the example according to the accompanying drawings, it is clear that the invention is not restricted to it, but may be varied in several ways within the scope of the inventive concept disclosed in the appended claims.

What is claimed is:

1. A measuring system which is arranged to measure the function of at least one organ from the user's body non-invasively and comprises at least one functional unit, including at least one of a transmitter unit and a receiver unit, wherein the at least one functional unit includes an induction coil for inductive interaction with another functional unit, a sound signaling device and a light source.

2. A system according to claim 1, wherein the system also comprises a data transmission unit and transmitter unit and the functional unit is a receiver unit, the data transmission unit being arranged to interact inductively with the receiver unit, the induction coil of the receiver unit being arranged for providing in addition to inductive interaction between the transmitter unit and the receiver unit and inductive interaction between the data transmission unit and the receiver unit, inductive interaction with the sound signalling device and the light source.

3. A system according to claim 1, wherein the functional unit is a receiver unit comprising at least a reception amplifier and receiver; power source; processor; one induction coil; control switches which open or close the connection of the induction coil at least to the reception amplifier, and a controller of the control switches which is arranged to control the switches so that the induction coil is used for only one inductive interaction at a time in the following manner:

when a signal is being received the controller of the control switches is arranged to close the switches to the reception amplifier and to keep the other switches open so that the induction coil is connected only to the reception amplifier, which is arranged to guide the amplified signal to the receiver and further to the processor.

4. A system according to claim 3, wherein the switches are transistor switches.

5. A system according to claim 1, wherein the functional unit is a receiver unit which comprises at least a transmission controller; power source; processor; one induction coil; control switches which open or close the connection of the induction coil at least to the transmission controller, and a controller of the control switches which is arranged to control the switches so that the induction coil is used for only one function at a time in the following manner:

when signals are being sent, the controller of the control switches is arranged to close the switches to the transmission controller and to keep the other switches open so that the induction coil is in contact only with the transmission controller, to which the processor is arranged to transfer the data to be sent.

6. A system according to claim 1, wherein the functional unit is a receiver unit which comprises at least a power source; light source controller and light source based on electroluminescence; one induction coil; control switches which open or close the connection of the induction coil at least to the light source controller, and a controller of the control switches which is arranged to control the switches so that the induction coil is used for only one function at a time in the following manner:

when the light of the light source is switched on, the controller of the control switches is arranged to close the switches to the light source controller and to the pole of the power source and to keep the other switches open so that the induction coil is in contact both with the light source controller and the pole of the power source, which is arranged to generate the electric power needed by the light source.

7. A system according to claim 1, wherein the functional unit is a receiver unit which comprises at least a power source; controller of a sound signalling device and piezoelectric sound signalling device; one induction coil; control switches which open or close the connection of the induction coil at least to the controller of the sound signalling device, and a controller of the control switches which is arranged to control the switches so that the induction coil is used for only one function at a time in the following manner:

when a sound signal is given, the controller of the control switches is arranged to close the switches to the controller of the sound signalling device and to the pole of the power source and to keep the other switches open so that the induction coil is in contact both with the controller of the sound signalling device and the pole of the power source, which is arranged to generate the electric power needed by the sound signalling device.

8. A system according to claim 1, wherein the functional unit is a transmitter unit which comprises at least a transmission controller; power source; processor; one induction coil; control switches which open or close the connection of the induction coil at least to the transmission controller, and a controller of the control switches which is arranged to control the switches so that the induction coil is used for only one function at a time in the following manner:

when signals are sent, the controller of the control switches is arranged to close the switches to the transmission controller and to keep the other switches open so that the induction coil is in contact only with the transmission controller, to which the processor is arranged to transfer the data to be sent.

9. A system according to claim 1, wherein the functional unit is a transmitter unit which comprises at least a power source; light source controller and light source based on electroluminescence; one induction coil; control switches which open or close the connection of the induction coil at least to the light source controller, and a controller of the control switches which is arranged to control the switches so that the induction coil is used for only one function at a time in the following manner:

when the light of the light source is switched on, the controller of the control switches is arranged to close the switches to the light source controller and the pole of the power source and to keep the other switches open so that the induction coil is in contact both with the light source controller and the pole of the power source, which is arranged to generate the electric power needed by the light source.

10. A system according to claim 1, wherein the functional unit is a transmitter unit which comprises at least a power source; controller of the sound signalling device and piezoelectric sound signalling device; one induction coil; control switches which open or close the connection of the induction coil at least to the controller of the sound signalling device, and a controller of the control switches which is arranged to control the switches so that the induction coil is used for only one function at a time in the following manner:

when a sound signal is given, the controller of the control switches of arranged to close the switches to the controller of the sound signalling device and to the pole of the power source and to keep the other switches open so that the induction coil is in contact both with the controller of the sound signalling device and the pole of the power source, which is arranged to generate the electric power needed by the sound signalling device.

11. A system according to claim 1, wherein the functional unit is a transmitter unit which comprises a chargeable power source, and the system comprises a charging device which comprises an inductance, and the transmitter unit comprises an inductance which is arranged to be used for charging the chargeable power source of the transmitter unit and for data transmission between the transmitter unit and the receiver unit by means of inductive interaction.

12. A system according to claim 1, wherein the functional unit is a receiver unit which comprises a chargeable power source, and the system comprises a charging device which comprises an inductance and is arranged to charge the chargeable power source of the receiver unit in inductive interaction with the receiver unit, and the receiver unit comprises an induction coil via which the receiver unit is arranged to perform at least two functions of the receiver unit.

* * * * *